United States Patent [19]
Politi et al.

[11] Patent Number: 5,447,951
[45] Date of Patent: Sep. 5, 1995

[54] METHOD FOR REDUCING THE LEVEL OF GLUCOCORTICOIDS IN THE BLOOD AND PREVENTING CEREBRAL DISTURBANCES

[75] Inventors: Vincenzo Politi; Mario Materazzi; Giovanni Di Stazio; Giovanna De Luca, all of Rome, Italy

[73] Assignee: Polifarma S.p.A., Roma, Italy

[21] Appl. No.: 179,203

[22] Filed: Jan. 10, 1994

[30] Foreign Application Priority Data

Jan. 25, 1993 [IT] Italy .................................. 93 A034

[51] Int. Cl.$^6$ .................................................. A01N 45/38
[52] U.S. Cl. ................................... 514/419; 514/415
[58] Field of Search .............................. 574/419, 415

[56] References Cited

U.S. PATENT DOCUMENTS

| | | | |
|---|---|---|---|
| 4,551,471 | 11/1985 | De Luca et al. | 514/419 |
| 4,808,728 | 2/1989 | De Luca et al. | 548/502 |
| 5,002,963 | 3/1991 | De Luca et al. | 514/419 |
| 5,075,329 | 12/1991 | Politi et al. | 514/415 |
| 5,091,172 | 2/1992 | Politi et al. | 424/59 |

FOREIGN PATENT DOCUMENTS 0106813  4/1984  European Pat. Off. .

OTHER PUBLICATIONS

Medline Abst 90:135126 of J. Cardiovasc Pharmacol. (1990 Jan.) 15(1) 102-8.
Fuller et al. (1976) Life Sciences vol. 19, pp. 337-346.
Bruni et al. (1982) Life Sciences vol. 30, pp. 1247-1254.
Popova et al. (1972) Brain Research vol. 47, pp. 61-67.
Nakagami et al. (1986) Brain Research vol. 386, pp. 232-236.
Chustecka (1988) *Scrip's Serotonin Report* pp. 1-3.
Sjoerdsma et al. (1990) Annals N.Y. Acad. of Sci. (600) pp. 1-8.
Biagini et al., Biol. Psychiatry, vol. 33, No. 10, pp. 712-719 (1993).
Sapolksy and Meaney: "Maturation of the Adrenocortical Stress Response . . . " Brain Res., Rev. 11, 65-67, 1986.
Spence et al: "Aging of the Brain" Ed. Karger, 37-51, 1991.
Dalbende et al: "Glucocorticoids, Transmitters and Stress" Brit. J. Psych. 160, Suppl. 15, 24-34, 1992.

*Primary Examiner*—Paul J. Killos
*Attorney, Agent, or Firm*—Birch, Stewart, Kolasch & Birch

[57] ABSTRACT

3-indolepyruvic acid is an active agent in preventing cerebral damage caused by stress and ageing and induced by an excessive presence in the blood of glucocorticoids, secreted by the adrenal gland.

5 Claims, No Drawings

METHOD FOR REDUCING THE LEVEL OF GLUCOCORTICOIDS IN THE BLOOD AND PREVENTING CEREBRAL DISTURBANCES

1. Background of the Invention

The present invention relates to an active agent in the prevention of cerebral damage caused by stress and ageing, and induced by an excessive presence in the blood of glucocorticoids secreted by the adrenal gland.

The active agent according to the invention is 3-indolepyruvic acid and its pharmaceutically acceptable salts.

2. Description of the Prior Art

It is well known from the literature that 3-indolepyruvic acid is present in all cells, both vegetable and animal, in balance with the amino acid tryptophan, from which it is produced by action of numerous enzymes, collectively known as aminotransferase.

3-indolepyruvic acid can be advantageously used both in treatment of diseases caused by a low concentration of serotonin in the brain (U.S. Pat. Nos. 4,551,471 and 4,808,728), in those deriving from an excess of excitatory amino acids (U.S. Pat. No. 5,075,329), and in peripheral diseases, in particular cardio-vascular diseases (U.S. Pat. No. 5,002,963). Furthermore, 3-indolepyruvic acid can also be used as a cosmetic agent to protect the skin against free radicals (U.S. Pat. No. 5,091,172).

It has now been found, and forms the object of the present invention, that 3-indolepyruvic acid can also be an effective active agent to prevent the neuron decay seen during prolonged periods of stress and which, according to a more and more widely accepted theory, leads to the disturbances in memory and behaviour seen in physio-pathological ageing.

During recent years, the relationship between stress and ageing has been studied, and the role played by glucocorticoids in the organism's response has been made extremely clear.

See, for example, Sapolsky and Meaney: Brain Res. Rev. 11, 65–76, 1986; Spence et al.: Ageing of the brain, Ed. Karger, 37–51, 1991; Dalbende et al.: Brit. J. Psych. 160, suppl. 15, 24–34, 1992. In particular, it has been seen that, in mammals, stress of any type provokes a response by the hypothalamus, which releases the hormone CRF (Corticotropin Releasing Factor). This hormone, in turn, causes the pituitary body to release the hormone ACTH (Adrenocorticotrophic Hormone). The ACTH entering the blood stream reaches the adrenal gland, where it causes the release of glucocorticoids, in particular corticosterone.

This well-known manner of activation of the response to stress is also known as the HPA (Hypothalamic-Pituitary-Adrenal) Axis.

The glucocorticoids have numerous and important effects on the cells of all tissues: they block immune and inflammatory responses, stimulate the formation of the enzymes employed in intermediate metabolism, prevent the pick-up of glucose from the blood stream, etc. In other words, the glucocorticoids can be seen as catabolizing hormones which, alongside the catecholamines, put the organism into a state of alert, ready to react to environmental stimuli either by attacking or escaping. In physiological situations, the glucocorticoids are released into the blood with a circadian rhythm, and maximum levels can be seen at the start of the animal's period of activity, which in man corresponds to the morning.

Because of their nature, glucocorticoids can be dangerous, as they require large-scale energy consumption without allowing the cell to refuel with the materials required to produce this energy. For this reason, the presence of glucocorticoids in the blood for long periods of time would risk causing the degeneration, and subsequently the death, of the cells over stimulated by the hormones. For this reason, mammals have a sophisticated re-balancing system: when a stress stimulus (either physical or pathological) arrives, a large amount of glucocorticoids is put into circulation and, on arrival in the central nervous system (and in particular in the hippocampus), it binds to receptors present there and sends an inhibitory signal (feed-back inhibition) to the hypothalamus to block any further secretion of CRF.

In this way acute stress is blocked, the secretion of glucocorticoids returns to a minimum and the organism can return to its normal functions.

In pathological situations, on the other hand, when the stress stimulus is repeated continuously, the glucocorticoid levels in the blood remain high for many hours or even days, and the neurons in the hippocampus, which are unable to neutralize the glucocorticoids sufficiently, begin to degenerate and die. This starts a chain reaction in which the reduced number of neurons in the hippocampus find it more and more difficult even to deal with the corticosteroids released during small daily stress events. In effect, it has been seen that in old animals the return of the glucocorticoids to minimum levels after stress stimulation is much slower than in young animals. Furthermore, in patients suffering from Alzheimer's disease (pathological ageing), higher levels of glucocorticoids can be seen than in other people of the same age.

All the above teaching has brought about the elaboration of the so-called "Sapolsky's theory" on cerebral aging, according to which the progressive decline in learning and memorizing abilities (located above all in the hippocampus) seen in elderly people, depends largely on continual stress, which causes a progressive loss of neurons from the hippocampus, which control the secretion of glucocorticoids.

High levels of activity of the latter would then act as a multiplying factor for degeneration, also acting as an immune suppressant.

SUMMARY OF THE INVENTION

An object of the present invention is therefore to provide a therapeutical agent which, by blocking excessive secretion of glucocorticoids by the adrenal gland, can also antagonize the harmful effects of stress and protect the brain from the degeneration seen during physio-pathological ageing.

It has been found that 3-indolepyruvic acid has shown itself capable of reducing corticosterone levels in the blood following stress events, and it therefore represents an agent for the treatment of the effects of stress on the central nervous system.

The object of the present invention is therefore the use of 3-indolepyruvic acid and pharmaceutically acceptable salts thereof for the preparation of a medicament to reduce the level of glucocorticoids in the blood.

The use of 3-indolepyruvic acid according to the invention is therefore aimed at the treatment of acute or chronic physical or psychological stress, as well as the prevention of disturbances due to senility and involving reductions in cerebral capabilities, such as insufficient memory, learning ability, behaviour and the like.

PHARMACOLOGICAL TESTS

In the following description the experimental results obtained when using 3-indolepyruvic acid according to the present invention will be shown.

EXAMPLE 1

Effect of 3-indolepyruvic acid (IPA) on psychogenic stress.

The experiment used 40 male Wistar rats (Nossan), weighing 280–300 g, kept in controlled stabling conditions. The rats were divided into 4 groups of 10 animals each: two groups received 100 mg/kg of IPA orally three times a day (every 8 hours). One of these groups, plus another control group, were made to undergo psychogenic stress, consisting in being handled and placed in an unknown environment for 15 minutes, one hour after administration of the last dose.

The animals were then decapitated using a guillotine, and the amounts of corticosterone present in the blood collected were found by radio-immunological assay.

The results obtained are given in the following table 1.

TABLE 1

| Animals No. | Group | Corticosterone (mcg/100 ml) |
|---|---|---|
| 10 | Control, no stress | 6.8 ± 2.5 |
| 10 | Control, with stress | 29.8 ± 3.5 |
| 10 | IPA, no stress | 10.8 ± 2.2 |
| 10 | IPA, with stress | 18.8 ± 2.2* |

*$p<0.01$ with respect to controls with stress.

EXAMPLE 2

Effect of 3-indolepyruvic acid (IPA) on physical stress caused by cold.

The animals (40 male Wistar rats) were divided and treated with IPA as in the experiment illustrated above.

Cold stress was caused in 20 animals (10 treated and 10 not), by placing them in a fridge (4° C.) for one hour. They were then decapitated using a guillotine, and the amounts of corticosterone present in the blood found.

The results are shown in the following Table 2.

TABLE 2

| Animals No. | Group | Corticosterone (mcg/100 ml) |
|---|---|---|
| 10 | Control, no stress | 6.0 ± 2.3 |
| 10 | Control, with stress | 35.8 ± 3.8 |
| 10 | IPA, no stress | 9.0 ± 2.9 |
| 10 | IPA, with stress | 28.0 ± 2.0* |

*$p<0.05$ with respect to controls with stress.

EXAMPLE 3

Effect of 3-indolepyruvic acid (IPA) on the blood corticosterone levels of rats subject to chronic stress.

32 Sprague-Dawley rats (Charles River) were kept in controlled stabling. They were then divided into 4 groups, two of which underwent a chronic stress procedure, as described below, while the other two acted as controls. Two groups (one undergoing stress and the other not) were treated with IPA (20 mg/kg/ip once a day), whereas the other two received the relative solvent.

The chronic stress was produced using the following methods in a random sequence: electric shock lasting 5 seconds; no food or water for one day; immersion in water at a temperature of 4° C. for 10 minutes; inversion of the day/night rhythm for 72 hours; exposure on a hot plate at 55° C. for 30 seconds.

After 3 weeks the animals were anaesthetized using ketamine (100 mg/kg/ip) and a blood sample was taken after 5 minutes by cardiac puncture. It was kept at 37° C. for 30 minutes and then centrifuged to separate off the serum, which was kept at −20° C. until radio-immunological dosing of corticosterone.

The results are given in the following table 3.

TABLE 3

| Animals No. | Group | Corticosterone (mcg/100 ml) |
|---|---|---|
| 8 | Solvent, no stress | 9.1 ± 2.4 |
| 8 | Solvent, with stress | 26.5 ± 1.6 |
| 8 | IPA, no stress | 11.4 ± 2.2 |
| 8 | IPA, with stress | 9.8 ± 3.5* |

*$p<0.01$ with respect to the solvent with stress group.

EXAMPLE 4

Effect of 3-indolepyruvic acid (IPA) on the corticosteroid receptors in the hippocampus.

The Sprague-Dawley rats used in the previous experiment and under anaesthetic were perfused with 100 ml of warm physiological solution, then with 100 ml of 4% paraformaldehyde. The brains were rapidly dissected and placed in contact with the same fixative solution (paraformaldehyde) for 12 hours. After washing with saccharose solution, the brains were sectioned with kryotome into slices 50 microne thick, and these were reacted with monoclonal antibodies specific for the glucocorticoid receptors.

Evaluation of the presence of receptors was performed on the dorsal area of the hippocampus, using an automatic image analyzer (Zeiss, Münich, Germany), capable of providing information on the total immunoreactivity (TIR) present in cubes 0.6 mm square.

The results are shown in the following table 4.

TABLE 4

| Animals No. | Group | Receptors (TIR) |
|---|---|---|
| 8 | Solvent, no stress | 415 ± 40 |
| 8 | Solvent, with stress | 590 ± 45 |
| 8 | IPA, no stress | 285 ± 20* |
| 8 | IPA, with stress | 315 ± 15** |

*$p<0.01$ with respect to the group solvent, no stress
**$p<0.01$ with respect to the group solvent, with stress.

Comment on the results of the pharmacological tests.

In the above examples, 3-indolepyruvic acid (IPA) clearly shows itself capable of reducing the levels of corticosterone in the blood of rats undergoing acute and chronic stress, both physical and psychological. Furthermore, IPA has been shown to influence the level of corticosterone receptors present in the hippocampus, not only in animals suffering from stress, but also in those used as controls, and this proves that IPA acts not only on the hypersecretion of corticosteroids caused by stress, but also on the mechanisms that influence the basic release of these compounds.

Treatment with IPA can therefore be therapeutically effective both in acute and chronic stress situations and when desiring to reduce the damage caused by corticosteroids in cerebral ageing.

3-indolepyruvic acid can be administered in the usual pharmaceutical forms, and in particular orally.

We claim:

1. A method for the treatment of disorders due to an increase of the glucocorticoid level in the blood of mammals which comprises administering to the mammal in need thereof a therapeutically effective amount of 3-indolepyruvic acid or a pharmaceutically acceptable salt thereof.

2. A method for preventing disturbances of the central nervous system caused by an excessive presence in the bloodstream of a mammal of glucocorticoids secreted by the adrenal gland which comprises administering to the mammal in need thereof a therapeutically effective amount of 3-indolepyruic acid or a pharmaceutically acceptable salt thereof.

3. A method as claimed in claim 2, in which said disturbances are situations of acute or chronic stress, both physical and physiological.

4. A method as claimed in claim 2, in which said disturbances are a decrease in cerebral capabilities due to senility.

5. A method as claimed in claim 4, in which said decrease in cerebral capabilities is loss of memory or learning ability behavior.

* * * * *

UNITED STATES PATENT AND TRADEMARK OFFICE
CERTIFICATE OF CORRECTION

PATENT NO. : 5,447,951
DATED : September 5, 1995
INVENTOR(S) : Vincenzo POLITI, Mario MATERAZZI, Giovanni Di STAZIO and Giovanna DeLUCA It is certified that error appears in the above-indentified patent and that said Letters Patent is hereby corrected as shown below:

Column 6, line 5, change "physiological" to --psychological--.

Signed and Sealed this

Twenty-fifth Day of June, 1996

Attest:

BRUCE LEHMAN

Attesting Officer     Commissioner of Patents and Trademarks